United States Patent
Hall et al.

(10) Patent No.: US 6,169,259 B1
(45) Date of Patent: *Jan. 2, 2001

(54) PORTABLE DEVICE FOR ELECTRICALLY DESTROYING NEEDLES

(76) Inventors: Robert M. Hall, 1006 Battery Lane Rd., Nashville, TN (US) 37220; Elton Clark, 4433 Plymouth-Sorrento Rd., Apopka, FL (US) 32712

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/834,561

(22) Filed: Apr. 7, 1997

Related U.S. Application Data

(63) Continuation-in-part of application No. 08/455,891, filed on May 31, 1995, now abandoned.

(51) Int. Cl.[7] .............................. B23K 11/22; A61G 12/00; A61L 11/00
(52) U.S. Cl. .............................................. 219/68
(58) Field of Search .............................. 219/68

(56) References Cited

U.S. PATENT DOCUMENTS

| | | | |
|---|---|---|---|
| 3,015,014 | * 12/1961 | Gartner et al. | 219/68 |
| 4,102,656 | 7/1978 | Kortiz . | |
| 4,628,169 | 12/1986 | Ch'ing-Lung . | |
| 4,707,338 | 11/1987 | Spector . | |
| 4,877,934 | 10/1989 | Spinello . | |
| 4,961,541 | * 10/1990 | Hashimoto | 219/68 |
| 4,965,426 | 10/1990 | Colombo . | |
| 5,046,669 | 9/1991 | Wallace et al. . | |
| 5,076,178 | 12/1991 | Kohl et al. . | |
| 5,091,621 | * 2/1992 | Butler | 219/68 |
| 5,138,124 | * 8/1992 | Kirk et al. | 219/68 |
| 5,138,125 | * 8/1992 | Salesses | 219/68 |
| 5,166,488 | * 11/1992 | Peppard | 219/68 |
| 5,212,362 | * 5/1993 | Burden et al. | 219/68 |
| 5,264,675 | * 11/1993 | Butler | 219/68 |
| 5,268,549 | * 12/1993 | Butler | 219/68 |
| 5,276,297 | * 1/1994 | Nara | 219/68 |
| 5,288,964 | 2/1994 | Walker et al. . | |
| 5,336,862 | 8/1994 | Yelvington . | |
| 5,391,849 | * 2/1995 | Furuya et al. | 219/68 |
| 5,468,928 | 11/1995 | Yelvington . | |
| 5,637,238 | * 6/1997 | Truesdale et al. | 219/68 |
| 5,676,859 | * 10/1997 | Yanobu | 219/68 |

FOREIGN PATENT DOCUMENTS

| | | |
|---|---|---|
| 2211420 | * 7/1989 | (GB) . |
| 2260707 | * 4/1993 | (GB) . |
| 2273231 | * 6/1994 | (GB) . |
| 6-343667 | * 12/1994 | (JP) . |

* cited by examiner

Primary Examiner—Geoffrey S. Evans
(74) Attorney, Agent, or Firm—Kilpatrick Stockton LLP

(57) ABSTRACT

An improved device for efficiently and safely destroying used hypodermic needles is disclosed. The needle destroying device is portable, operating from a battery power pack, and makes use of a capacitor that discharges current into any needle inserted into the device for destruction. The strong discharge of current completely destroys small needles and substantially speeds up destruction of medium or large needles. An apparatus for adjusting the device to accept different sized needles is also provided. The adjusting apparatus ensures that small needles adequately contact the electrodes located within the device and that large needles do not wear down or separate the electrodes. A motor may also be provided and coupled between the battery and a fan. The motor drives the fan to pull air into the device and thereby circulate it through a filter, located in a removable tray within a cartridge, that prevents vapors or particles from exiting the device. The filter is infused with disinfectant that kills any airborne pathogens. Also, the motor may couple to one of the electrodes in order to move the electrode and propel from the electrode slag formed during the destruction process. A converter that changes direct current from a battery or other portable power supply to alternating current may be provided. Alternating current more efficiently destroys the needles while extending battery charge and life.

27 Claims, 5 Drawing Sheets

PORTABLE DEVICE FOR ELECTRICALLY DESTROYING NEEDLES

CROSS-REFERENCE TO RELATED APPLICATION

This application is a continuation-in-part of U.S. application Ser. No. 08/455,891, filed May 31, 1995, now abandoned, which application is hereby incorporated in its entirety by this reference.

This invention relates to improved apparatus for safely and efficiently destroying used hypodermic needles.

BACKGROUND OF THE INVENTION

Used hypodermic needles often contain residues of potentially dangerous materials, such as blood carrying HIV, hepatitis B or other infectious diseases. Because the sharp tips of the needles may prick the skin of persons attempting to dispose of them, many devices are available for destroying the needles. Some of such devices utilize incineration apparatus that generate electric currents that destroy the needle, crushing apparatus that grinds and crushes the needle and the syringe housing, or apparatus using a combination of both incineration and crushing.

For example, U.S. Pat. No. 5,076,178 to Kohl, et al. discloses a needle incineration device. Insertion of the needle to be destroyed pushes a carriage unit that couples to an electrical power source for sending a high voltage electric current through the carriage unit and into the needle. However, "carriage movement is limited to insure that an operator does not attempt to incinerate the entire length of an extraordinarily long needle in a single operation and thereby exceed power capacity limits." Like the device disclosed by Kohl, et al., other devices such as the one described in U.S. Pat. No. 4,628,169 to Ch'ing-L'ung exist that require the user carefully to feed the needle into the apparatus to ensure destruction of the needle. Similarly, U.S. Pat. No. 4,877,934 to Spinello disclose a device that is "self-powered" through an optional rechargeable battery and that also requires the user to feed progressively shorter lengths of a needle into the device in order for incinerating currents to destroy the needle. Thus, using the Spinello or Ch'ing-L'ung devices, it is likely that a hurried or careless user could destroy only part of the needle, leaving a dangerous "stub."

Such careful feeding is further complicated by the fact that needles come in a variety of sizes. If too large a needle is being destroyed, the destruction device may not develop sufficient current to destroy the needle completely or destruction may take a long time. Similarly, if too small a needle is being destroyed, the electrodes of an incinerator-type destruction device may be too far apart to allow the needle to close the circuit between the electrodes. Furthermore, constant use of the device may wear down the electrodes, further separating them, or may leave the electrodes coated with the "slag" created during destruction of a needle. Thus, current will either not flow or flow only intermittently from the electrodes into the needle, thereby leaving all or parts of the needle intact.

Moreover, even if the needle is adequately destroyed, there may be some residue of material from the needle or the syringe left inside the destruction device. Thus, U.S. Pat. No. 4,961,541 to Hashimoto indicates that "a disinfectant may be sprayed onto the syringe during the collapsing operation." However, spraying each syringe is time consuming and easily forgotten in the press of other duties. Also, there is no provision for eliminating airborne emissions during destruction of the needle. Without proper precautions and/or a sufficiently fast destruction process, airborne pathogens may leave the hollow needle before, during or after the destruction process.

Additionally, for each of the above-described devices, the user apparently must carry the needle to the device for destruction. This activity increases the risk that medical personnel or others inadvertently may prick themselves with a needle before it is destroyed. U.S. Pat. No. 5,046,669 to Wallace, et al. recognizes that collecting used hypodermic needles for destruction entails significant problems. Wallace, et al. thus provides a collection unit and a centrally located processing unit that both breaks the needle into fragments and melts the plastic syringe housing.

It would also, however, be desirable to have a compact, portable device that can, for instance, be moved to locations where blood is being taken or vaccinations given, remote from health care facilities or that can be transported within a larger medical facility by a nurse or orderly making rounds. Other than the "self-powered" Spinello device that only incrementally destroys needles and does not appear to foreclose airborne emissions, no truly portable, compact and inexpensive destruction devices are available, however. Instead, many of the destruction devices are outfitted with numerous "bells and whistles," such as bulky transformers for coupling the device to a main power supply or infrared sensors for activating the device, that add complexity and cost. Such complexity is entirely unnecessary for many users, who simply desire to completely destroy their needles before disposal. Exemplary of such users are diabetics and dentists, both of which groups make use of very small and fine needles. While these persons desire to dispose of used needles properly, the high cost of the overly complex destruction devices dissuades such proper disposal.

SUMMARY OF THE INVENTION

The present invention addresses the above problems by providing a portable device that can be used in a variety of locations, may have a self-contained power source, fully destroys needles of various lengths and gauges in one step, and sterilizes and/or prevents escape of pathogens and potential contaminants. Additionally, one embodiment of the present invention provides a simple and inexpensive needle destruction device that is capable of destroying instantly and completely small needles such as those used by dentists or diabetics.

Briefly, the present invention is a portable needle destroying device provided with a power supply such as a replaceable or rechargeable battery, perhaps provided with a transformer for converting A.C. to D.C., an adjustable dial that is used to set the gap between two electrodes in order to allow needles of varying gauge to be used with the device, and a filter infused with disinfectant that prevents particulate or airborne pathogens from escaping from the device. The battery may be rechargeable. Instead, however, of connecting directly to one of the electrodes, the battery may couple to an energy storing device such as an inductor, capacitor or thyristor circuit. The storage device is charged by the battery and holds a charge for release when a needle is inserted and creates a short circuit across the gap between the electrodes. The released charge, or arc, is powerful enough to destroy small needles completely without requiring the user to insert successively smaller lengths of the needle into the device in order to ensure the needle's destruction. Alternatively, even for large needles, the released charge significantly speeds the destruction of the needle and the battery may also supply power to the electrodes so that complete destruction of larger needles is quickly completed following initial insertion and release of the stored charge.

The device accommodates needles of all lengths and gauges by providing a means for adjusting the gap between the electrodes. The adjusting means is controlled by a dial that the user turns to move an adjustable electrode. Turning the dial in one direction decreases the bias of a spring to allow the adjustable electrode to move away from a second electrode and thereby more efficiently accept a larger needle. Turning the dial in the other direction increases the spring bias and forces the adjustable and second electrodes closer together to accept a smaller needle. Absent such adjustment it is exceedingly difficult for the user completely to destroy all of the needle. If the gap were too large for a small needle, likely the user would be forced to rock the needle back and forth to ensure complete contact between the needle and electrodes. Such rocking possibly would be insufficient and leave a dangerous, sharp "nub" of needle. Alternatively, if the gap were too small, use of larger needles would more quickly wear down the electrodes, ultimately possibly causing electrode failure or at least leading to replacement of the electrode sooner than otherwise necessary.

In one embodiment, the power supply may couple to a motor that optionally rotates the second electrode in order to remove the slag produced during destruction of the needle, as is generally shown and described in U.S. Pat. No. 5,138,124 to Kirk, et al., which is hereby incorporated in its entirety by this reference. When the power supply is a battery, a direct current ("dc") motor should be used. Because the motor may be actuated when the user slides a needle into the device and thereby electrically connects the adjustable and second electrodes and causes release of the stored charge, a high starting torque motor (like a dc motor) may be used in order to begin immediately rotating the second electrode. Immediate rotation ensures that the "slag" or other residue produced by the destruction of the needle is thrown into a disposable cartridge by the rotation of the second electrode rather than attaching to, and decreasing the effectiveness of, the electrodes.

In an alternative embodiment, the second electrode is a flat plate with at least one slanted edge. A moving or vibrating means couples to the plate for reciprocating the plate back and forth, thus causing the slag to flow down the sides of the plate and effectively cleansing the electrode. The movement or vibration need not result in great displacement of the electrode, although vibrating the electrode at a high frequency, and beveling one edge of the electrode, may assist in dislodging substantially all of the slag. One such vibrating means may be a buzzer circuit, which utilizes a coil to produce a magnetic field that pulls a metallic strip toward the coil. When the strip is moved away from its resting plate, a short is created between the coil and its power supply, resulting in the strip returning to its resting place, at which point the circuit is energized and the strip is again pulled from its resting place. (The frequency of the buzzer circuit can be adjusted by changing the amount of field produced by the coil or the spring characteristics of the strip). By coupling one end of the strip to an electrode, the electrode will reciprocate back and forth as the strip is moved back and forth. Another moving means may simply be a motor whose shaft rotates and eccentric weight, which causes the motor to vibrate. Mechanically coupling the motor to the electrode translates the vibration into the electrode.

While the motor may be used to move the electrode, its shaft may also couple to a fan that pulls smoke, dust or particle-laden air through a case holding the battery, motor, electrodes and a disposable cartridge. The air is channeled through the disposable cartridge, which is sealed via a gasket to the side of the case in order to prevent smoke, dust or particles from entering the case that surrounds the motor. The air travels through a filter that is impregnated with a disinfectant and loaded into a removable tray to allow replacement of the filter or replenishment of the disinfectant. The disinfectant both cleanses contaminates from the air and deodorizes the emissions caused by vaporization of the residues left in the needle. A timer on a control board that couples to the motor ensures the motor operates for a predetermined interval so that the fan will pull sufficient air into the cartridge to prevent any of the vapors and fumes generated from the destruction of the needle from escaping unfiltered and unfreshened via the impregnated filter.

In another embodiment, the device comprises a case that encloses a battery that may be coupled to an energy storing circuit, a first electrode and a second electrode. Either of the first or the second electrodes may be provided with the adjusting means adjustor that allows the user to adjust the gap between the first and second electrodes in order to size the gaps for accepting needles of different sizes. The energy storing device may comprise a capacitor, inductor or a thyristor circuit that may couple to the battery, store a charge, and instantly release the stored charge when a needle is inserted through a hole in the case and contacts both electrodes. If the needle is small enough, the released charge normally destroys the entire metallic tip of the needle virtually instantaneously. This embodiment is thus particularly useful for destroying "double-ended" needles that have a first needle portion with a sharpened tip extending outside the syringe body and a second needle portion that extends through a hub and into the body of the syringe. Normally, because the second portion of the needle is surrounded by the syringe, destruction of the needle requires an inconvenient, two-step process, whereby the user first destroys the sharpened, first portion of the needle, then removes the hub and destroys the second portion of the needle that extends into the syringe body. Utilizing the energy storing device, however, allows the present invention to generate a sufficiently powerful arc and discharge that the entire length of the needle (e.g., both the first and second portions) is destroyed upon insertion of the needle into the hole for contacting the two electrodes.

A recharge pack can be provided for use with the battery. LEDs may be used to indicate whether the battery needs a recharge or when the capacitor will be recharged and ready to destroy another needle. Furthermore, in order to increase the flexibility of the device and allow it to interface with wall outlets and the like that source A.C., a regulated power supply that converts A.C. power to a 12 volt supply may be provided. This embodiment is particularly useful for situations in which many needles are being destroyed daily.

Yet another embodiment of the present invention uses a converter to change direct current ("D.C.") provided by the power supply to an alternating current ("A.C.") that is then supplied to at least one of the electrodes. There are a number of advantages to providing such a D.C. to A.C. converter. First, A.C. current provides an improved oxidation or burn of the needle during its destruction. The oxidation is faster—perhaps as much as 60% faster for use with some larger needles—and, because of the more rapid destruction process, the unit emits fewer sparks to surprise unwary users. Essentially, providing such A.C. current means that the electrodes act as a "welder". By contrast, D.C. current has a tendency to "blow off" chips of the needle, which results in a rougher burn. Second, an A.C. current also improves the life of the portable power pack or battery between recharges. Less current is pulled from the battery during the oxidation process because of the "on" and "off" current cycles being supplied to needle destroying electrodes; further, during the "off" cycle, the battery may recover from the current drain. This leads to less battery abuse during oxidation, an increased number of needles that each battery charge can destroy, a faster recovery time between destruction of two needles, and an extended life overall for the battery.

A preferred embodiment of the D.C. to A.C. converter uses a conversion circuit that essentially acts as a timing circuit to turn the current on and off at a selected frequency to create an alternating square wave. For instance, a timer can actuate multiple transistors, such as MOSFETs, to change D.C. current to an A.C. current that is supplied to a needle destroying electrodes. Setting the timer to provide a current alternating in a frequency range of from about 400 to 800 Hertz may result in optimum needle destruction with less noise that creates appropriately-sized needle particles.

Determined that during the destruction of a needle, the supply voltage may decrease enough that the control circuits may not be powered. A charging circuit may therefore be provided to couple to the power supply in order to power the control board during needle destruction.

In short, the present invention provides a device for safely and efficiently destroying completely a hypodermic needle of virtually any size and preventing the escape of vapor, dust, particles or air-borne emissions upon destruction of the used needle. Apparatus for removing slag from the electrodes is provided, thereby maximizing the performance of the electrodes. A portable, inexpensive version of the invention can be used to destroy completely small needles, including double-ended needles.

It is accordingly an object of the present invention to provide a portable device for destroying needles.

It is another object of the present invention to couple a power supply to an energy storage device that provides a discharge sufficiently powerful to at least partially destroy a used needle.

It is a further object of the present invention to provide a dial coupled to a gap adjustor for properly sizing the gap between electrodes that convey electric currents to the needle to be destroyed.

It is an additional object of the present invention to provide a filter impregnated with disinfectant for thoroughly cleansing vapors and other contaminates released upon destruction of a used needle.

It is yet an additional object of the present invention to provide a D.C. to A.C. converter that transforms battery D.C. current to A.C. current, which when supplied to the needle destroying electrodes, more efficiently destroys needles while extending battery charge and life.

It is still another object of the present invention to provide a timing circuit for converting D.C. current supplied by the battery to A.C. current supplied to the electrodes.

It is still a further object of the present invention to provide a charge circuit for powering the control circuit during needle destruction.

Other objects, features and advantages of this invention will become apparent with reference to the remainder of this document.

DETAILED DESCRIPTION OF THE DRAWINGS

Figure 1:
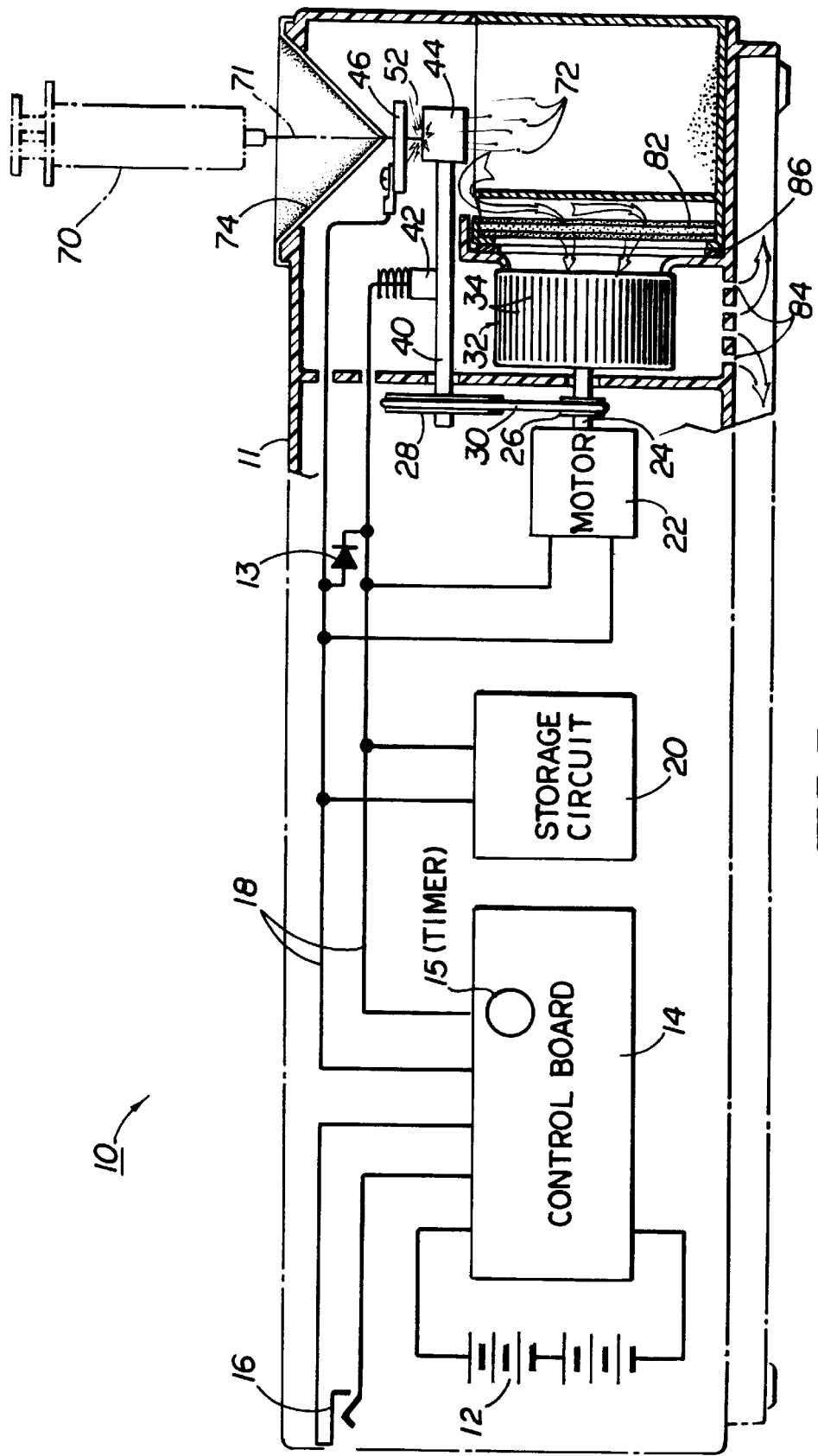
FIG. 1 is a schematic diagram of the components of one embodiment of the present invention.

FIG. 1 shows in a schematic block diagram one embodiment of the portable needle destruction device 10 of the present invention. A case 11 encloses a power supply such as a battery 12 that couples to a control board 14 that includes a timer 15. A recharging outlet 16 may be provided to allow the device 10 to be plugged into a recharging device in order to replenish the battery 12. Power lines 18 lead from the control board 14 to a charge or energy storage circuit 20 and then to a motor 22. Storage circuit 20 typically consists of a capacitor, although other devices such as an inductor or a thyristor circuit may also be used. LEDs 13 may also be provided on the outside of the case to indicate to the user whether the battery 12 needs to be recharged or whether the storage circuit 20 has recharged and the device 10 is thus ready to accept and destroy another needle.

Motor 22 drives a motor shaft 24 that rotates a first pulley wheel 26 and a paddle-wheel fan 32 that has a number of slats 34. An o-ring belt 30 couples the first pulley wheel 26 to a second pulley wheel 28, which in turn drives an electrode shaft 40. Forming the first and second pulley wheels 26 and 28 from a plastics material, such as phenolic, and using an o-ring belt 30 ensures that if a user jams a needle 70 into the device 10, the pulley wheels 26 and 28 will stop while the motor 22 overload initiates.

At the end of the electrode shaft 40 is a rotating electrode 44. Power is transferred to the rotating electrode 44 via brush 42 that couple the power lines 18 to the conductive electrode shaft 40. Although the brush 42 could abut the end of the electrode shaft 40, placing the brush 42 on the side of the electrode shaft 40 ensures better power transfer. Alternatively, the brush 42 could couple directly to the rotating electrode 44, with a channel separating the brush 42 from the end of the rotating electrode 44 to prevent needle residue from interfering with the power transfer accomplished by the brush 42.

Figure 2A:
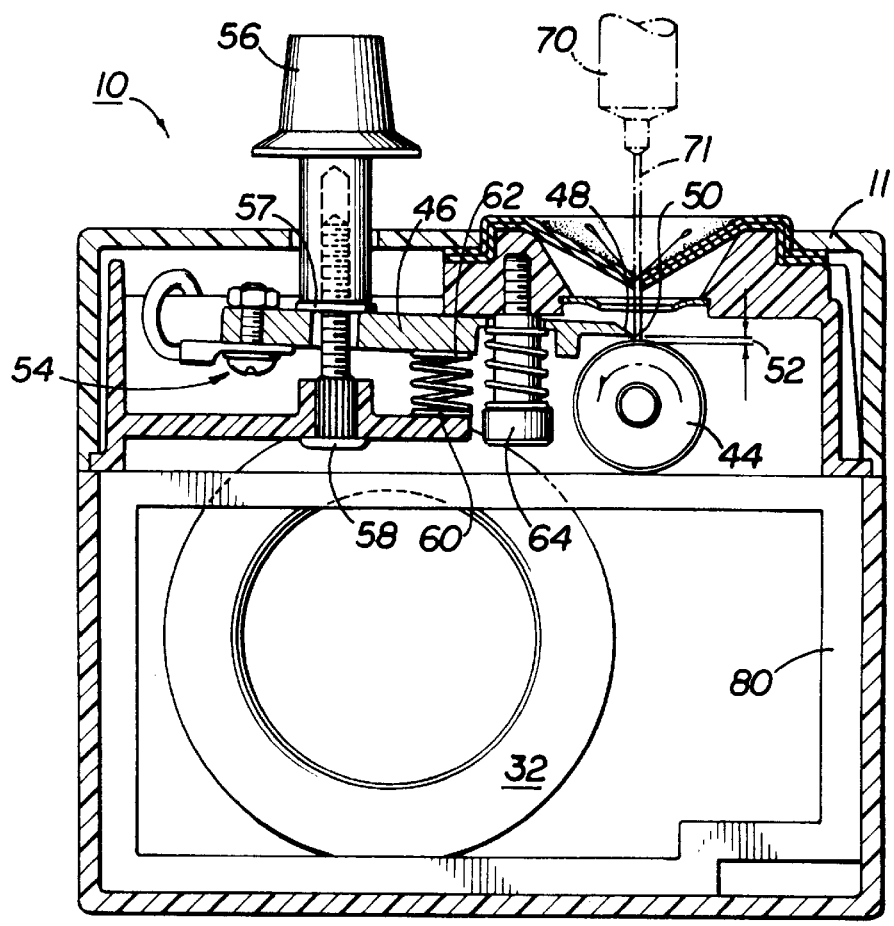
FIG. 2A is a side view of one embodiment of the present invention provided with an adjustable and a rotating electrode with the adjustable electrode set for accepting a small needle.
Figure 2B:
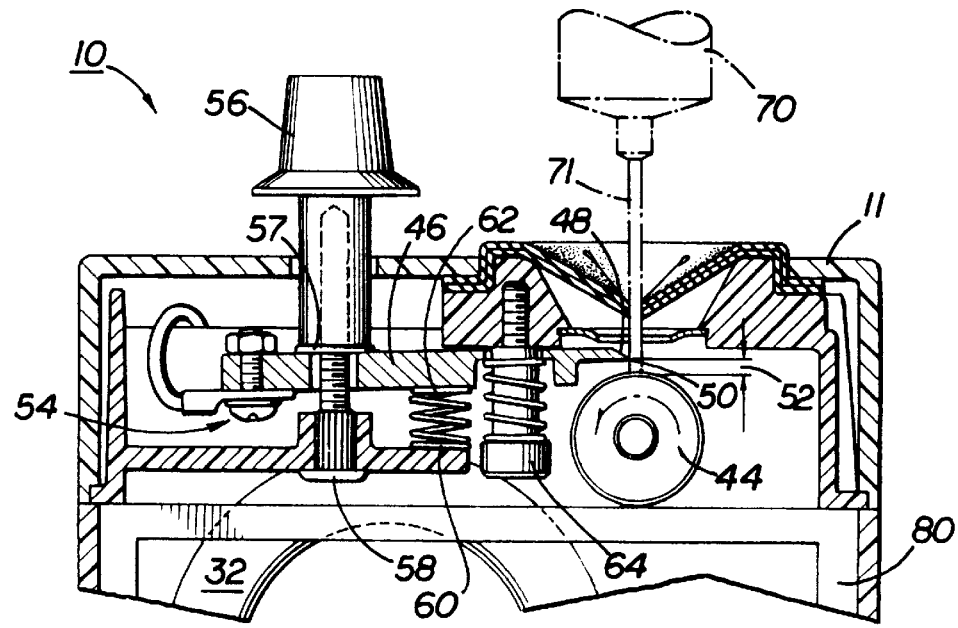
FIG. 2B is a side view of the embodiment shown in FIG. 2B with the adjustable electrode set for accepting a large needle.

An adjustable electrode 46 is separated from the rotating electrode 44 by a gap 52, as can perhaps best be seen in FIGS. 2A and 2B. A gap adjusting means 54 allows the user to turn a dial 56 and adjust the gap 52 between the rotating electrode 44 and the adjustable electrode 46, which is biased by a spring 60 to bear against a fulcrum 62. A spring-loaded set screw 64 is used to set the initial size of the gap 52. Rotating the dial 56 causes it to go up or down a threaded screw 58; the end 57 of the dial 56 thus is moved toward or away from the adjustable electrode 46. Because the spring 60 biases the other end of the adjustable electrode 46 upwards, moving the dial 56 moves the end 57 up or down, causing the adjustable electrode 46 to pivot toward nor away from the rotating electrode 44. Alternatively, if the geometry of the case 11 does not allow placement of the dial 56 directly over the adjustable electrode 46, a second length of material could connect between the end 57 of the dial 56 and the adjustable electrode 46 in order to transfer the force generated by turning the dial 56 into motion of the adjustable electrode 46.

Adjustable electrode 46 defines a bevel 48 that ends in a tip 50 for concentrating electric potential and delivering the current into a metallic needle tip 71 once the needle tip 71 is inserted through an opening 68 in the case 11 and contacts both the adjustable and rotating electrodes 46 and 44. A guide 74 is 20 provided that may be generally funnel shaped and spring-loaded with a spring wrapped around flexible portions that open farther depending on the size of the needle 70 being inserted into the opening 68. Guide 74 ensures that the needle tip 71 is brought directly to the gap 52 for destruction. Thus, the guide 74 eliminates the need to "rock" back and forth the needle tip 71 do in order to achieve contact between the needle tip 71 and the electrodes. Guide 74 also hides sparks created during the destruction process from the user and decreases the possibility that waste created during destruction will be thrown through the opening 68 and possibly onto the user's hands.

Contact of the needle tip 71 with the electrodes essentially closes an open circuit consisting of the electrodes in parallel with the storage circuit 20 and the battery 12. Closing the circuit causes the storage circuit 20 immediately to discharge and create an arc across the electrodes that destroys the needle tip 71. About six (6) volts from the battery 12 has been found sufficient to destroy most needles 70, particularly since the storage circuit 20 initially greatly multiplies the effective current transfer through the electrodes into the needle 70.

Delivery of current into the needle tip 71, which has a high electrical resistance, heats and melts the needle tip 71 into the slag 72. Rotation of the rotating electrode 44 throws the slag 72 down into a cartridge 80 and also "pulls" the needle tip 71 further into the device 10. Use of a shield, located inside the case 11, to surround the rotating and adjustable electrodes 44, 46 may further ensure that the slag 72 is directed down into the cartridge 80 and does not escape back through the opening 68. Although much of the residue left in the needle tip 71 after use will be destroyed by the current, some smoke, vapor or dust will be generated. Guide 74 and a shield may prevent much of this material from escaping back out of the opening 68; however, absent operation of the fan 32 much of this material will escape.

Fan 32 pulls air through the opening 68 and into the cartridge 80. The air is laden with the emissions from the destruction of the needle tip 71 and is channeled into a filter 82, which is impregnated with a strong disinfectant both to sterilize any pathogens that may have been in the needle tip 71 and not destroyed, and to freshen the air. Filter 82 may be formed of multiple membranes that better trap particles of varying sizes. In order to allow replenishment of the disinfectant or replacement of the filter 82, it is held in a removable tray that can easily be inserted in and removed from the case 11. Alternatively, a door or sliding access hatch could also be used to gain access to the tray holding the filter 82. After passing through the filter 82, the now deodorized air exits the case 11 through exhaust vents 84. A gasket 86 prevents unfiltered air from passing through the cartridge since allowing unfiltered air through not only results in odorous emissions from the case 11 but also may result in the motor 22 being clogged by the particles found in the unfiltered air.

Figure 3:
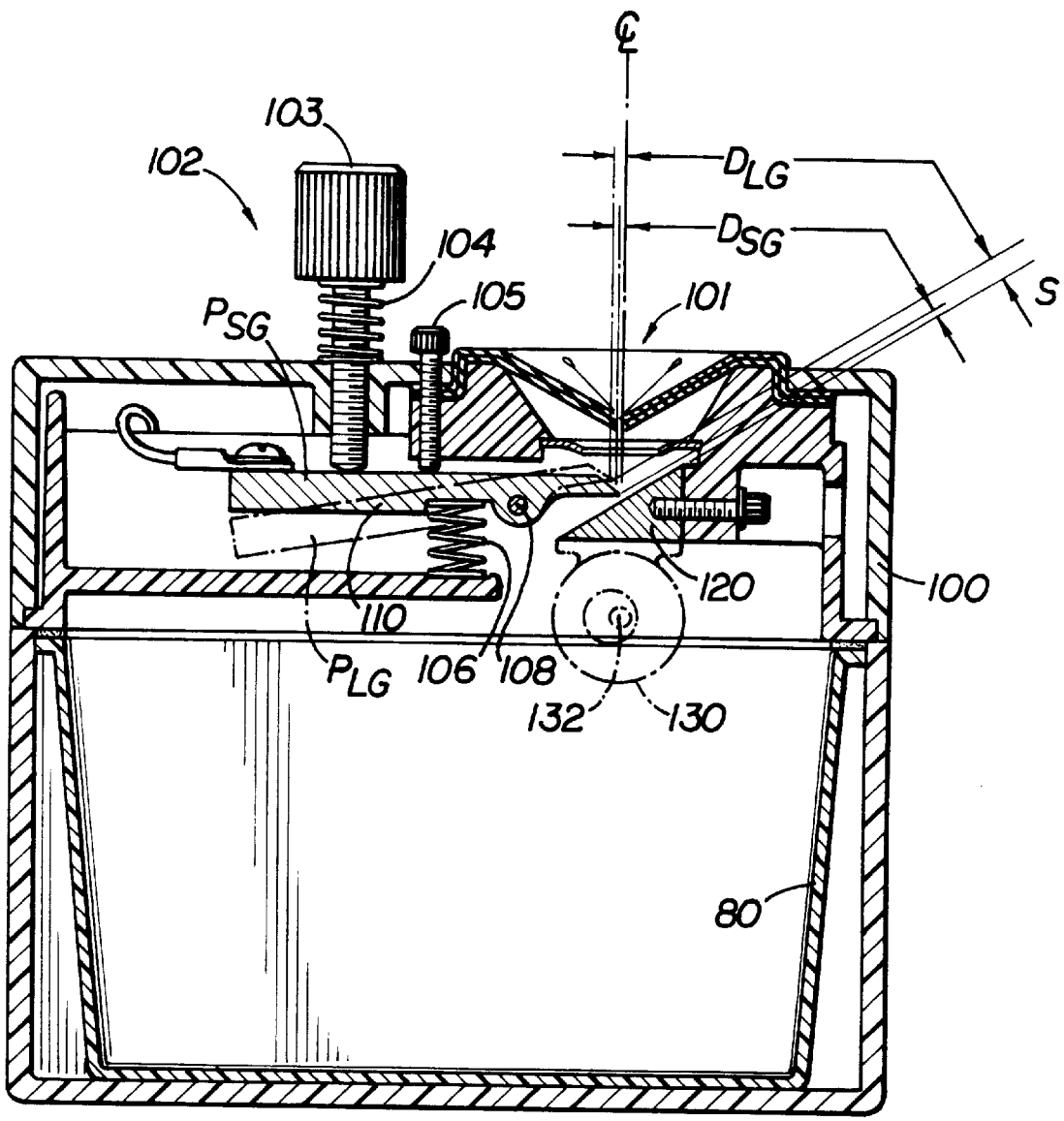
FIG. 3 is another embodiment of the present invention provided with an adjustable electrode and a vibrating electrode plate.

FIG. 3 shows an embodiment of the present invention provided with a case 100 enclosing another adjusting means 102 for adjusting the distance between a movable electrode 110 and a conductive plate 120. Case 100 also surrounds and contains a power supply, which may be either a battery 12 or a transformer that may couple to a main power supply via a conventional plug and cord, a storage circuit 20 and a motor 130. (Optionally, the filtration system, comprising a fan and a filtered cartridge may also be placed within the case 100). Note that if the transformer is provided, the power supply then comprises a plug to couple to a wall outlet or the like and a transformer that converts the A.C. to a D.C. Case 100 can be formed to allow the transformer power supply to plug into the same terminals that a battery 12 would occupy. This is useful to allow the user temporarily to make the device 10 a fixed station that can destroy numerous needles; thereafter, the battery can be replaced and the device 10 becomes portable.

Movement or vibration of the vibrating plate 120 ensures that slag 72 does not build up upon the surfaces of the vibrating plate 120 that acts as an electrode for conducting current to a needle tip inserted through a hole 101 in the case 100 for destruction. Vibration can be accomplished by mounting the high rpm motor 130 to the vibrating plate 120. Placing an eccentric weight 132 on the motor shaft causes the motor to vibrate and the vibration is mechanically transmitted to the vibrating plate 120. Vibration also may be accomplished by spring-loading vibrating plate 120, attaching a cam to a rotating shaft driven by the motor 130 and abutting a cam against one end of the plate 120. Rotation of the cam will translate into mechanical vibration of the spring-loaded vibrating plate 120.

Alternatively, vibrating plate 120 could be constrained in a channel or track and have one end coupled to a vibrating means that will reciprocate the vibrating plate 120 back and forth within the track in order to remove slag that may otherwise attach to the vibrating plate 120. One such reciprocating means may be a buzzer circuit, although any means for moving the vibrating plate 120 may also be used. Additionally, a cleaning mechanism may be provided for allowing the user to clean the vibrating plate 120 off. The cleaning mechanism may be a blade located adjacent to the track and capable of being moved, preferably by the user, close to the track in order to "wipe" the vibrating plate 120 free of slag or other residue after destruction of one or more needle(s). Alternatively, the cleaning mechanism may simply be an adjustable block, one surface of which is a cleaning surface that may be brought into contact with the vibrating plate 120 and either be manually moved across the surface of the vibrating plate 120 or held against its surface during vibration or movement of the vibrating plate 120.

A set screw 105 can be used to set the initial gap between the movable electrode 110 and the vibrating plate 120, which may be shaped in the form of a triangle with one of the legs abutted against and loosely attached to the case 100. The gap 50 can be widened or narrowed by manipulating the adjusting means 102 to reorient the movable electrode 110 from a position suitable for destroying a small gauge needle (whose diameter is Dsg), indicated by Psg, to a position suited for destroying a large gauge needle (whose diameter is Dlg), indicated by position Plg. Adjusting means 102 may operate by having a user turn a dial 103 to select a needle size. Turning the dial 103, which may be loaded with spring 104, forces the end of a set screw 105 down against the back of the movable electrode 110. The force applied by the set screw 105 overcomes the bias spring 106, causing the movable electrode 110 to pivot about pivot point 108.

The initial position of the movable electrode 110 is partially determined by the amount of vertical displacement vibration causes in plate 120. In order to ensure that the plate 120 does not inadvertently touch movable electrode 110 during vibration, it may be necessary to vibrate the plate only along its horizontal axis. A lead may be secured to the vibrating plate 120 and the movable electrode 110 for conveying current to the electrode 110 and plate 120. Insertion of a needle into the hole 101 causes destruction of the needle tip. Resulting slag 72 or other debris is shaken from the plate 120 via vibration and falls into the cartridge 80 that may be provided with the disinfectant-impregnated filter 82.

Figure 4:
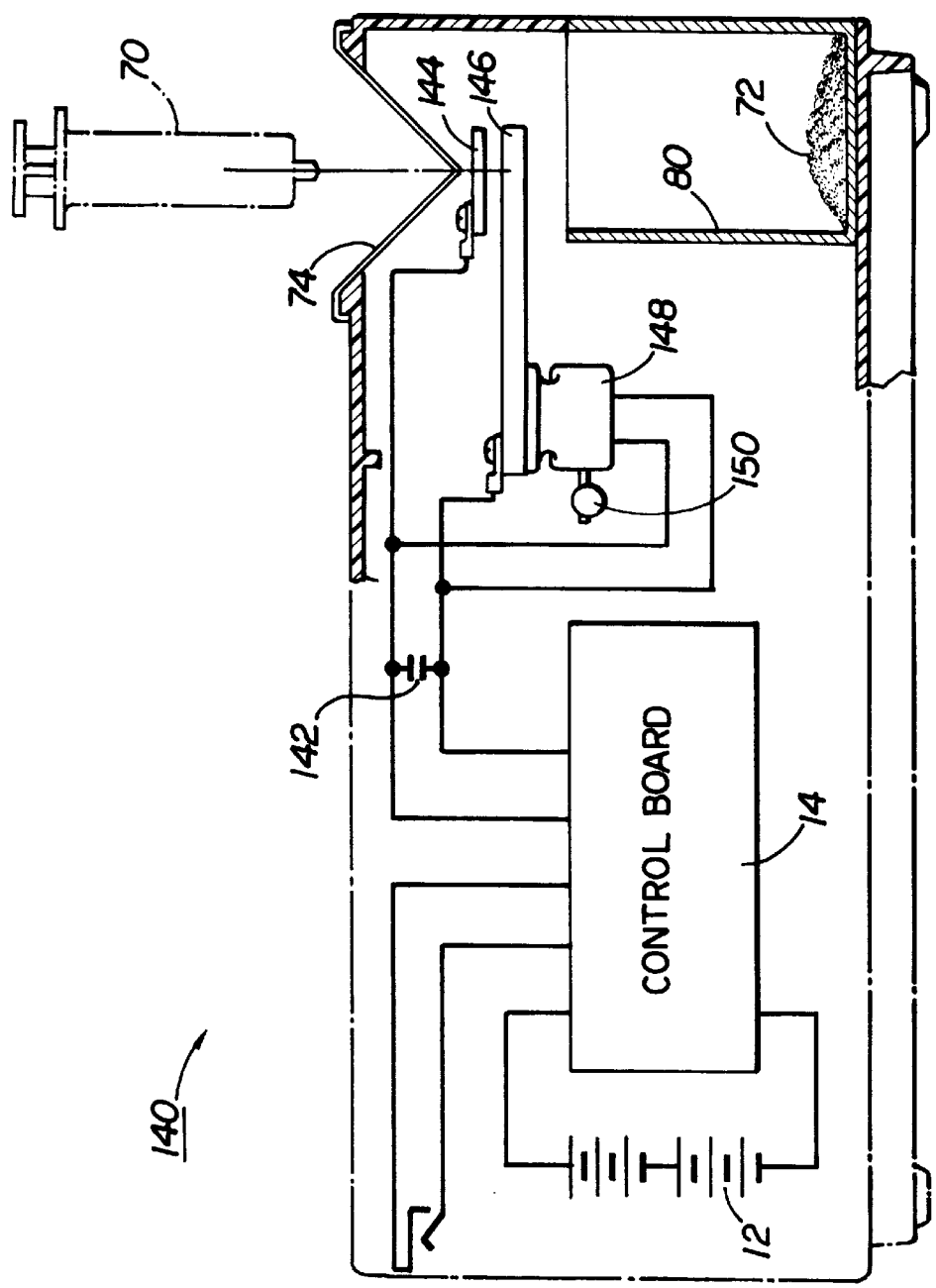
FIG. 4 is a schematic diagram of the components of a portable and inexpensive embodiment of the present invention provided with a storage circuit for supplying a large, almost instantaneous discharge to destroy small needles.

An additional embodiment is shown in FIG. 4. This simple, portable device 140 is provided with a battery 12, coupled to a capacitor 142 and power lines 18 that lead to first and second electrodes 144, 146. Note that the first and second electrodes 144, 146 may be fixed or second electrode 146 may be coupled to a slag removing means 148 that, possibly through operation of the motor 150 on command of the control board 14, moves the second electrode 146 to cause slag to fall off of the second electrode and into the cartridge 80. However, the slag removing means 148 is totally optional for this embodiment since it is designed for very small needles that the capacitor 142 generally will be alone sufficient substantially to destroy.

Figure 5A:
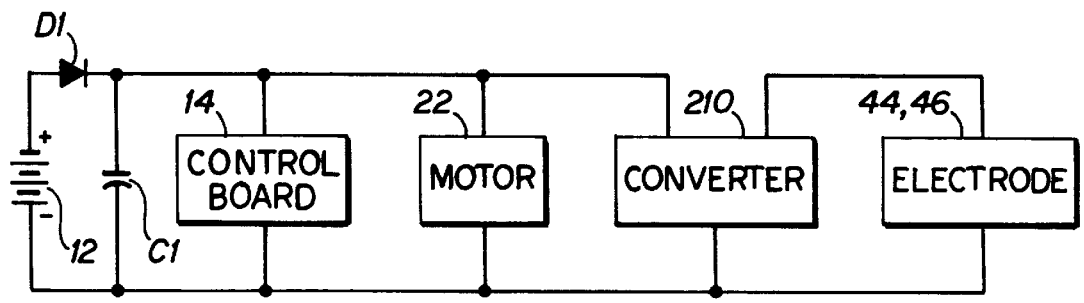
FIG. 5A is a block diagram showing one embodiment of the present invention equipped with a converter.

FIG. 5A shows a block diagram of the present invention equipped with a converter 210. A battery 12 supplies current to one or both electrode(s) 44, 46 through diode D1 and capacitance C1 to the control board 14, motor 22, and D.C. to A.C. converter 200.

Capacitance C1 acts as an optional charge storage circuit for powering the control board 14 during needle destruction. As soon as device 10 turns on, a fast diode D1 that couples battery 14 and capacitance C1 allows current from the battery 14 to charge capacitance C1 that may comprise one or several coupled capacitors. As current drains from battery 12 into a particular needle, the battery 12 voltage level drops. However, C1 provides an additional charge to the control board 14 in order to power the circuits inside of device 10. For example, C1 may comprise enough capacitance to power the device 10 for about six seconds, which is enough time to destroy most needles.

Generally, converter 200 changes D.C. current from battery 12 to alternating current. For example, converter 200 creates an alternating signal in the range of about 200 to 800 Herz (Hz). That frequency suffices to destroy the average needle so as to create pellets of waste material. A higher frequency may create more noise or convert the needle to fine dust that can clog filter 82 or interfere with operation of motor 22. On the other hand, decreasing the frequency may likewise create more noise or it may create sparks or excessively large needle fragments. Also, a lower frequency may not provide sufficient "off" time to allow battery 12 to recover even while in use.

Figure 5B:
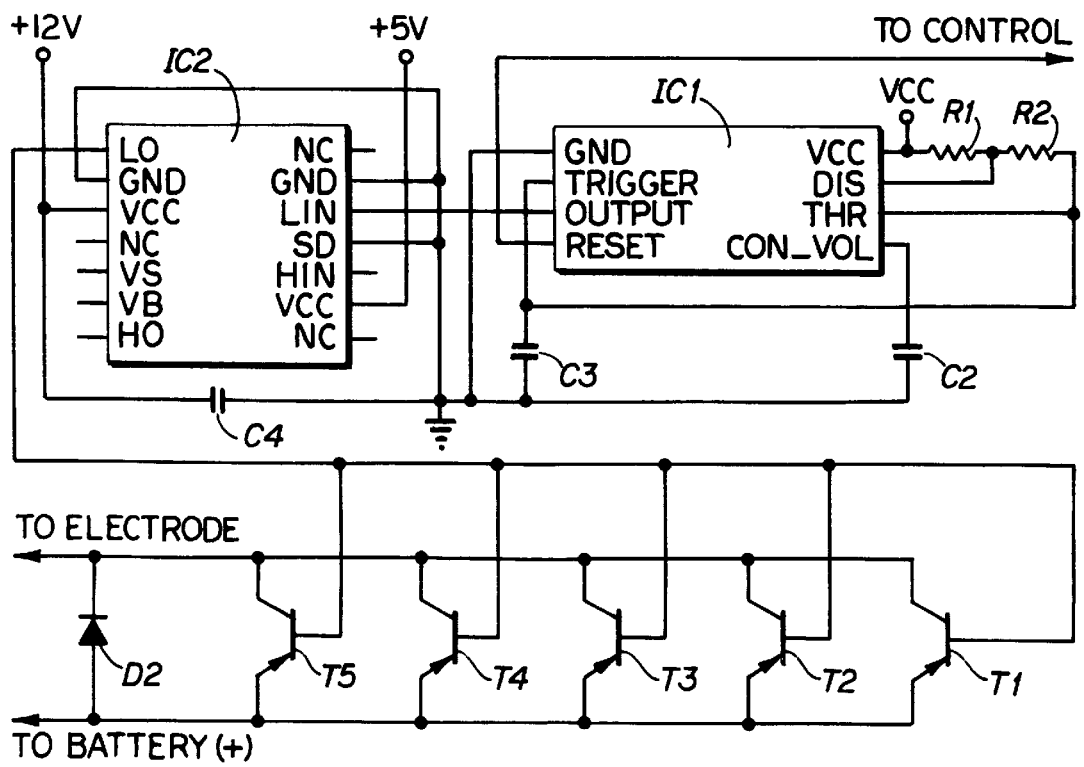
FIG. 5B is a circuit diagram showing one embodiment of the D.C. to A.C. converter shown in FIG. 5A.

Converter 200 can be formed from a series of transistors, such as MOSFET transistors T1, T2, T3, T4 and T5 connected in parallel and shown in FIG. 5B. If transistors T1–T5 are MOSFETs, they may be rated at 98 amperes of continuous drain each, although each transistor T1–T5 will handle about 70 amperes of current from battery 12 that generally supplies about 350 amperes. (Thus, the use of 5 transistors T1–T5). Other types or numbers of transistors T1–T-5 with different rated current capacity may be used.

In any event, in the FIG. 5B embodiment, a timer 210 turns transistor T1 on and off; that, in turn, activates the other transistors T2–T5. In operation, a control signal, such as from activation of an infrared pickup by a user's hand passing within range of a sensor, actuates an integrated timing circuit IC1, which may be an LM555 timer. IC1, in turn, outputs a timing signal whose frequency depends upon the setting of R2 and C3. In the particular embodiment shown in FIG. 5B, the IC1 output turns a driver, IC2, on and off. IC2, in turn, couples to T1's gate in order to turn it on and off. The output from each transistor T1–T5 thus looks similar to the output from IC1, creating an alternating current that applies through a diode D2 to electrode 44 or 46. D2 clips off spikes created when applying current through an electrode 44, 46 to a needle, thereby protecting the integrity of the alternating current signal from converter 200.

The converter 200 embodiment shown in FIG. 5B creates an on/off square wave (although the on and off times need not be symmetrical). Applying an A.C. signal to an electrode 44 or 46 in order to destroy a needle results in most of the needle "burn" or destruction occurring as the signal peaks. A square wave provides a more effective burn because it generates a peak "on" that supplies full power to the needle and an "off" that allows the battery 12 time to recover from the current drain. Additionally, during the "off" period transistors T1 through T5 dissipate heat generated during operation.

Of course, persons skilled in this art will recognize that converter 200 can be formed by circuit elements having a low D.C. resistance and capable of switching the D.C. current on and off. Likewise, a mechanical converter 200 could be provided. For example, rotating electrode 44 could be provided with strips of conducting and non-conducting material. A short circuit across battery 12 forms when a needle inserts across electrodes 44, 46, except that as electrode 44 rotated, the conducting strips would conduct to provide current while alternating non-conducting strips would not conduct, effectively creating alternating current.

The foregoing is provided for purposes of illustrating, explaining and describing several embodiments of the present invention. Modifications and adaptations to these embodiments—such as using different types of transistors or timing circuits to drive them—will be apparent to those of ordinary skill in the art and may be made without departing from the scope or spirit of the invention and the following claims.

What is claimed is:

1. Portable apparatus for destroying used hypodermic needles of varying sizes, the apparatus comprising:

(a) a case, defining an opening into which a needle may be inserted, the case at least partially surrounding a power supply coupled to a first and a second electrode, with the first electrode separated from the second electrode by a gap located substantially adjacent the opening; and (b) means, accessible at least partially from the exterior of the case, for adjusting the vertical height of the gap between the first and second electrodes in order to accommodate needles of varying sizes so that, upon insertion of a needle into the opening, the needle electrically contacts the first and second electrodes, whereupon an electric current discharges, converting at least a portion of the needle into slag.

2. Portable apparatus according to claim 1 in which the first electrode is coupled to and moved by the adjusting means and the second electrode is a plate and further comprising means for moving the plate in order to remove a substantial portion of the slag.

3. Portable apparatus according to claim 1 further comprising a filter, infused with disinfectant and located within the case, for deodorizing vapors released on destruction of the needle.

4. Portable apparatus according to claim 3 further comprising an aperture within the case for removably accepting the filter.

5. Portable apparatus according to claim 4 in which the power supply comprises a rechargeable battery.

6. Portable apparatus according to claim 1 further comprising a capacitor coupled to the power supply and the first and second electrodes.

7. Apparatus for destroying used hypodermic needles, the apparatus comprising:
   (a) a case defining a first opening into which a needle may be inserted and a second opening for accepting a cartridge;
   (b) a first electrode and a second electrode separated by a gap;
   (c) a means, accessible at least partially from the exterior of the case, for vertically adjusting the first electrode relative to the second electrode in order to vary the gap to accept the selected needle;
   (d) a filter, removably inserted into the cartridge, infused with disinfectant;
   (e) a battery for supplying power to a motor coupled to a fan and the first electrode; and
   (f) a capacitor comprising a first and second terminal with:
      i) the first terminal coupled to the battery; and
      ii) the second terminal coupled to the second electrode that is sufficiently close to the first electrode that insertion of a needle into the first opening causes the capacitor to discharge current through the first and second electrodes into the needle.

8. Portable apparatus for destroying used hypodermic needles of varying sizes, the apparatus comprising:
   (a) a case, defining an opening into which a needle may be inserted, the case surrounding a power supply coupled to a first and a second electrode, with the first electrode separated from the second electrode by a gap located substantially adjacent the opening;
   (b) a charge storing circuit coupled to the power supply and the first and second electrodes;
   (c) means operable via a dial associated with the case for adjusting the vertical height of the gap between the first and second electrodes in order to accommodate needles of varying sizes so that, upon insertion of a needle into the opening, the needle electrically contacts the first and second electrodes, whereupon the charge storing circuit discharges an electric current that converts at least a portion of the needle into slag and in which the first electrode is coupled to and moved by the adjusting means and the second electrode is a plate;
   (d) a filter, infused with disinfectant and located within the case, for deodorizing vapors released on destruction of the needle; and
   (e) means for moving the plate in order to remove a substantial portion of the slag.

9. Apparatus for destroying used hypodermic needles, the apparatus comprising:
   (a) a case defining a first opening into which a needle may be inserted and a second opening for accepting a cartridge;
   (b) a first electrode and a second electrode, wherein the second electrode comprises a substantially flat, beveled surface;
   (c) a means for adjusting the first electrode in relation to the second electrode in order to more efficiently discharge current into the needle;
   (d) a filter, removably inserted into the cartridge, infused with disinfectant;
   (e) a battery for supplying power to a motor coupled to a fan and the first electrode;
   (f) a capacitor comprising a first and second terminal with:
      i) the first terminal coupled to the battery; and
      ii) the second terminal coupled to the second electrode that is sufficiently close to the first electrode that insertion of a needle into the first opening causes the capacitor to discharge current through the first and second electrodes into the needle; and
   (g) a means for vibrating the second electrode.

10. Apparatus comprising:
    (a) a case, defining a hole through which a used hypodermic needle is inserted in order to destroy the needle;
    (b) a power supply;
    (c) a first electrode and a second electrode, each connected to the power supply, positioned substantially adjacent to the hole and located substantially close to one another to define a gap for accepting a selected needle;
    (d) means, coupled to the first electrode and operable from the exterior of the case, for vertically adjusting the first electrode relative to the second electrode in order to vary the gap to accept the selected needle, whereby insertion of the needle into the hole causes the release of a charge through the first and second electrodes and into the selected needle to thereby destroy at least a portion of the needle; and
    (e) means, coupled to the second electrode, for moving the second electrode to clean from the second electrode a substantial portion of any residue produced from the at least partial destruction of the needle.

11. Apparatus according to claim 10 further comprising means for controlling the operation of the moving means.

12. Apparatus according to claim 10 further comprising a filter impregnated with disinfectant and deodorizer and an aperture within the case for removably accepting the filter.

13. Apparatus according to claim 12 further comprising means for initially adjusting the gap between the first and second electrodes.

14. Apparatus according to claim 12 further comprising a fan, powered by a motor coupled to the power supply, for pulling air through the hole in the case, into the filter and out of an exhaust.

15. Apparatus according to claim 14 further comprising a timer for operating the motor for a predetermined period in order to ensure that the air surrounding the hole has been pulled into the case and filtered.

16. Apparatus according to claim 15 in which the power supply comprises a rechargeable battery.

17. Portable apparatus for destroying used hypodermic needles of varying sizes, the apparatus comprising:
    (a) a case, defining a hole through which a used hypodermic needle is inserted in order to destroy the needle;
    (b) a rechargeable battery;
    (c) an adjustable electrode and a movable electrode positioned substantially adjacent to the hole and located substantially close to one another to define a gap for accepting a selected needle;

(d) means, coupled to the adjustable electrode and operable from the exterior of the case, for vertically repositioning the adjustable electrode relative to the movable electrode in order to vary the gap to accept the selected needle, whereby insertion of the needle into the hole causes release of a charge through the movable and adjustable electrodes and into the selected needle to thereby destroy at least a portion of the needle;

(e) means, coupled to the movable electrode, for reciprocating the movable electrode to remove a substantial portion of residue produced from the at least partial destruction of the needle;

(f) a filter, removably inserted into the case, infused with disinfectant; and (g) a motor coupled to the battery and a means for circulating air surrounding the case into the filter.

18. Portable apparatus for destroying used hypodermic needles comprising:

(a) a case, defining an opening into which a needle may be inserted, the case surrounding a rechargeable battery coupled to a first and a second electrode, with the first electrode separated from the second electrode by a gap located substantially adjacent the opening;

(b) a gap adjuster, located so as to be operable without accessing the interior of the case, for vertically moving at least one of the first or second electrodes relative to the other to thereby accommodate needles of varying sizes so that, upon insertion of a needle into the opening, the needle electrically contacts the first and second electrodes, whereupon an electric current passes through at least one of the first or second electrodes into the needle and converts at least a portion of the needle into slag; and (c) a filter, infused with disinfectant and located within the case, for deodorizing vapors released on destruction of the needle.

19. Portable apparatus according to claim 18 further comprising a charge storing circuit coupled to the battery and the first and second electrodes, whereby the charge storing circuit discharges stored energy into the needle when the needle electrically contacts the first and second electrodes.

20. Portable apparatus for destroying used hypodermic needles comprising:

(a) a case, defining an opening into which a needle may be inserted, the case surrounding a rechargeable battery coupled to a first and a second electrode, with the first electrode separated from the second electrode by a gap located substantially adjacent the opening;

(b) a gap adjuster for moving at least one of the first or second electrodes relative to the other to thereby accommodate needles of varying sizes so that, upon insertion of a needle into the opening, the needle electrically contacts the first and second electrodes, whereupon an electric current passes through at least one of the first or second electrodes into the needle and converts at least a portion of the needle into slag;

(c) a filter, infused with disinfectant and located within the case, for deodorizing vapors released on destruction of the needle; and (d) a direct current to alternating current converter coupled to the battery and at least one of the first or second electrodes for discharging alternating current into the needle when the needle electrically contacts the first or second electrodes.

21. Portable apparatus for destroying used hypodermic needles of varying sizes, the apparatus comprising:

(a) a case, defining an opening into which a needle may be inserted, the case at least partially surrounding a power supply coupled to a first and a second electrode, with the first electrode separated from the second electrode by a gap located substantially adjacent the opening;

(b) means for adjusting the gap between the first and second electrodes in order to accommodate needles of varying sizes so that, upon insertion of a needle into the opening, the needle electrically contacts the first and second electrodes, whereupon an electric current discharges, converting at least a portion of the needle into slag, wherein the first electrode is coupled to and moved by the adjusting means; and (c) means for vibrating the second electrode, wherein the second electrode comprises a substantially flat, beveled surface and is coupled to the vibrating means.

22. Portable apparatus for destroying used hypodermic needles comprising:

(a) a case, defining an opening into which a needle may be inserted, the case surrounding a rechargeable power supply coupled to a first and a second electrode, with the first electrode separated from the second electrode; and (b) a direct current to alternating current converter coupled to the power supply for discharging alternating current into the needle when the needle electrically contacts the first and second electrodes, whereupon an electric current passes through at least one of the first or second electrodes into the needle and destroys at least a portion of the needle.

23. Portable apparatus according to claim 22 further comprising a charge storing circuit coupled between the power supply and a control circuit that automatically activates a motor for operating a fan for pulling air into a filter associated with the case.

24. Portable apparatus according to claim 22 further comprising:

(a) a gap adjustor for moving at least one of the first or second electrodes relative to the other to thereby accommodate needles of varying sizes; and (b) means for moving at least one of the first or second electrodes.

25. A method for destroying needles of varying sizes using an apparatus with at least two electrodes, the method comprising:

(a) vertically adjusting the relative positions of the at least two electrodes in order to vary the gap to accept a selected needle;

(b) inserting the selected needle into the apparatus so as to contact both electrodes;

(c) destroying at least a substantial portion of the needle by discharging energy from a power supply through the electrodes and into the needle; and (d) moving at least one electrode in order to remove a substantial portion of slag resulting from needle destruction.

26. The method according to claim 25, wherein the adjusting step further comprises the step of vertically repositioning the first electrode relative to the second electrode utilizing a gap adjuster to vary the distance between the two electrodes to thereby accommodate needles of various sizes.

27. A method for destroying needles of varying sizes using an apparatus with at least two electrodes, the method comprising:

(a) adjusting the relative positions of the at least two electrodes in order to vary the gap to accept a selected needle;

(b) inserting the selected needle into the apparatus so as to contact both electrodes;

(c) destroying at least a substantial portion of the needle by discharging current from a battery through the electrodes and into the needle, wherein a converter switches the battery current from direct to alternating current; and (d) moving at least one electrode in order to remove a substantial portion of slag resulting from needle destruction.

* * * * *